United States Patent [19]

Anderson et al.

[11] Patent Number: 5,753,575
[45] Date of Patent: May 19, 1998

[54] METHOD FOR REGENERATING A HYDROGEN FLUORIDE AND SULFONE ALKYLATION CATALYST

[75] Inventors: Richard L. Anderson; Bruce B. Randolph; Keith W. Hovis, all of Bartlesville, Okla.

[73] Assignee: Phillips Petroleum Company, Bartlesville, Okla.

[21] Appl. No.: 601,921

[22] Filed: Feb. 15, 1996

[51] Int. Cl.$^6$ .................... B01J 38/56; B01J 20/34
[52] U.S. Cl. ............................. 502/31; 502/29
[58] Field of Search ................. 502/29, 31; 585/724, 585/802, 857

[56] References Cited

U.S. PATENT DOCUMENTS

| | | | |
|---|---|---|---|
| 5,191,150 | 3/1993 | Child et al. | 585/809 |
| 5,264,651 | 11/1993 | Better et al. | 585/802 |
| 5,264,652 | 11/1993 | Child et al. | 585/802 |
| 5,463,162 | 10/1995 | Eastman | 585/724 |

*Primary Examiner*—Glenn Caldarola
*Assistant Examiner*—Alexander G. Ghyka
*Attorney, Agent, or Firm*—Charles W. Stewart

[57] ABSTRACT

Disclosed is an alkylation process which utilizes a mixture of sulfone and hydrogen fluoride as an alkylation catalyst. The process provides for the regeneration of an alkylation catalyst having ASO therein by separating HF from the ASO and sulfone components. The ASO and sulfone are thereafter separated to provide sulfone which is substantially free of ASO.

24 Claims, 2 Drawing Sheets

METHOD FOR REGENERATING A HYDROGEN FLUORIDE AND SULFONE ALKYLATION CATALYST

The present invention relates to a hydrocarbon conversion process for the alkylation of olefin hydrocarbons by isoparaffin hydrocarbons which utilizes a catalyst mixture comprising a sulfone compound and a hydrogen halide compound. More specifically, the invention relates to a process for removing acid soluble oil from the alkylation catalyst mixture used in an alkylation process system to prevent buildup of acid soluble oil in the alkylation catalyst mixture.

BACKGROUND OF THE INVENTION

It has recently been discovered that a mixture, comprising a sulfone compound and a hydrogen halide compound, can be an effective catalyst for use in the alkylation of olefin hydrocarbons by isoparaffin hydrocarbons to produce an alkylate reaction product, or alkylate. The alkylate reaction product generally contains hydrocarbons having five or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain unwanted polymeric reaction by-products such as those referred to as acid-soluble oils, or ASO. These polymeric reaction by-products are referred to as acid-soluble oils; because, they are soluble in the acid catalyst utilized in the alkylation process and, thus, remain in the acid catalyst phase when the alkylate product resulting from the contact of a hydrocarbon mixture with an alkylation catalyst is separated from the alkylation catalyst.

In an alkylation process that continuously separates the catalyst phase from the alkylation reaction product for reuse in the alkylation process reaction zone, there is a buildup of ASO which accumulates in the catalyst phase. Over time, the ASO concentration will reach an unacceptable level if not removed from the catalyst phase. A low concentration of ASO in the alkylation catalyst comprising a sulfone component and a hydrogen halide component is believed to have a beneficial effect upon the alkylation process or its product. However, a higher concentration in the alkylation catalyst has an adverse effect upon the catalyst activity and the final alkylate end-product. An ASO concentration in the alkylation catalyst that exceeds a certain acceptable limit will result in lowering the octane of the alkylate end-product with incremental increases in the ASO concentration in the alkylation catalyst phase causing incremental decreases in the alkylate octane.

In order to regenerate the alkylation catalyst by the removal of ASO, a portion of the alkylation catalyst is passed to a stripping vessel whereby the HF component is stripped from the sulfone and ASO components. The stripped HF component may be recombined with the alkylation catalyst; however, the sulfone with ASO must undergo a further separation to provide sulfone which is free of ASO so that it may be recombined with the alkylation catalyst. This separation is made difficult by the presence of HF and, in some instances, the presence of heavy hydrocarbons having six or more carbon atoms.

SUMMARY OF THE INVENTION

It is, therefore, an object of this invention to provide a novel method for removing ASO from a sulfone and hydrogen fluoride alkylation catalyst.

A further object of this invention is to provide a method for preventing the accumulation of ASO within an alkylation catalyst of a continuous alkylation process.

A still further object of this invention is to provide a method for regenerating an alkylation catalyst comprising a sulfone, hydrogen fluoride and ASO.

A yet further object of this invention is to provide a method for separating ASO from an ASO and sulfone mixture, which may contain HF or a hydrocarbon having at least six carbon atoms.

The present invention is a method for regenerating an alkylation catalyst mixture used in an alkylation process system. The alkylation catalyst mixture of the inventive method is taken from an alkylation process system and contains HF, sulfone, and an ASO reaction by-product containing light ASO and heavy ASO. A portion of the alkylation catalyst mixture is passed to means for stripping HF from the alkylation catalyst mixture to provide a stripper bottoms stream and a stripper overhead stream. The stripper overhead stream contains HF and the stripper bottoms stream contains sulfone and ASO reaction by-product. A concentration of isobutane of at least about 10 volume percent is provided in the stripper bottoms stream. The resultant stripper bottoms stream having the at least about 10 volume percent concentration of isobutane is subsequently separated into at least two liquid phases including an upper phase and a lower phase. The upper phase includes a major portion of the isobutane provided in the stripper bottoms stream and light ASO and the lower phase includes sulfone and heavy ASO. The lower phase undergoes a vacuum distillation in order to provide an overhead product containing sulfone and a bottoms product containing heavy ASO. The overhead product may be recombined with the alkylation catalyst mixture for reuse.

Figure 1:
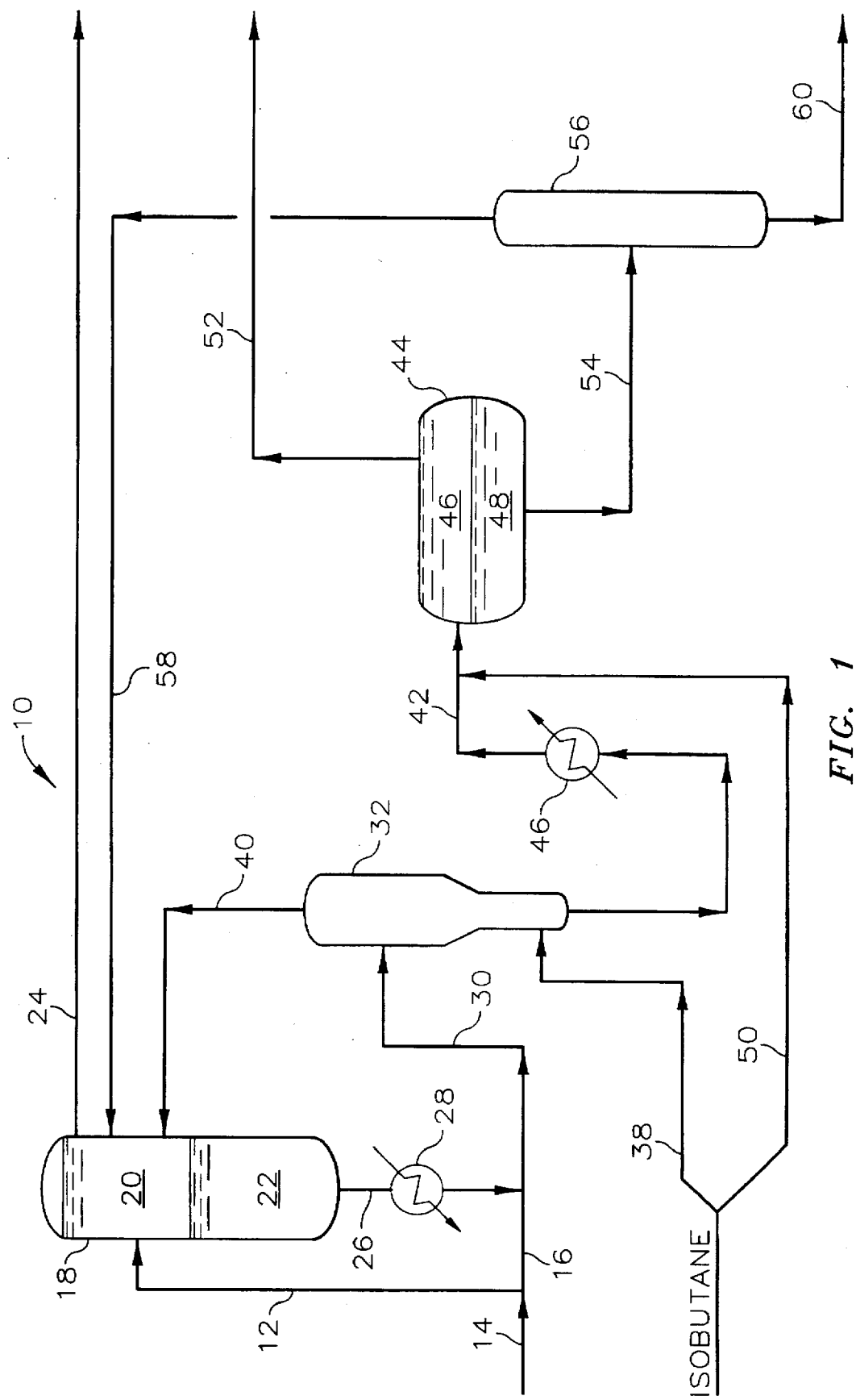
FIG. 1 is a schematic representation of the process which is one embodiment of the invention.

Other objects and advantages of the invention will be apparent from the detailed description of the invention and the appended claims.

DETAILED DESCRIPTION OF THE INVENTION

The acid soluble oil referred to herein is produced as a reaction by-product in an alkylation process comprising the step of contacting a hydrocarbon mixture, which comprises olefins and isoparaffins, with an alkylation catalyst, which comprises a hydrogen halide component and a sulfone component. As used within this description and in the appended claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1, (January 1963) by Miron and Lee. This article is incorporated herein by reference.

The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is more narrowly defined, ASO will be those conjunct polymers produced as a by-product in the catalyzed reaction of mono-olefins with isoparaffins utilizing a catalyst mixture comprising a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane and the preferred hydrogen halide component is hydrogen fluoride.

The ASO by-product derived from the hydrocarbon reaction catalyzed by a sulfone-containing alkylation catalyst can be further generally characterized as having a specific gravity, with water at 60° F. as the reference, in the range of from about 0.8 to about 1.0, an average molecular weight in the range of from about 250 to about 350, and a bromine number in the range of from about 40 to about 350. The boiling temperature of the ASO by-product can range from an initial boiling point of about 200° F. to an end-point of about 1100° F. This ASO by-product includes a light ASO portion and a heavy ASO portion. The term "light ASO", as used in this description and in the appended claims, refers to an ASO by-product having a 50 percent distillation point of less than about 660° F. and an end-point of less than about 1050° F. The term "heavy ASO", as used in this description and in the appended claims, refers to an ASO by-product having 50 percent distillation point of greater than about 650° F. and an end-point of greater than about 1050° F.

The hydrogen halide component of the alkylation catalyst composition or alkylation catalyst mixture utilized in the alkylation process can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water.

The sulfones suitable for use in this invention are the sulfones of the general formula $$R-SO_2-R'$$

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethyl-sulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as, for example, chloromethylethylsulfone. These sulfones may advantageously be used in the form of mixtures.

When sulfolane is used as the preferred sulfone, it can be utilized in the alkylation catalyst composition in anhydrous form, but, more often, the sulfolane component, when added to the alkylation catalyst composition as a make-up component, can have a small amount of water. Generally, the sulfolane component used to form the alkylation catalyst mixture will have a water concentration up to about 5 weight percent of the total weight of the sulfolane and water. However, preferably, the water contained in the sulfolane component will be in the range of from about 0.1 to about 5.0 weight percent of the total weight of the sulfolane and water and, most preferably, the water will be present in the range of from 0.5 to 4 weight percent.

In the alkylation process, the accumulation of water in the alkylation catalyst composition in no event can be more than about 10 weight percent of the total weight of the catalyst composition, which includes sulfone, hydrogen halide and water. Preferably, the concentration of water present in the alkylation catalyst composition is less than about 7.5 weight percent. Most preferably, the concentration of water present in the alkylation catalyst composition is less than 3 weight percent.

Thus, the alkylation catalyst composition used in the alkylation process system wherein an ASO reaction by-product is produced can comprise a hydrogen halide component and a sulfone component, both as described herein, and a concentration of water. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with a weight ratio of hydrogen fluoride to sulfolane in the alkylation catalyst in the range of from about 1:1 to about 40:1. A preferred weight ratio of hydrogen fluoride to sulfolane can range from about 1.2:1 to about 19:1 and, more preferably, it can range from 1.5:1 to 9:1.

In order to improve selectivity of the alkylation reaction of the present invention toward the production of the desirable highly branched aliphatic hydrocarbons having five or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

In the alkylation process, the reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. A portion of the catalyst can continuously be regenerated or reactivated as described herein, or by any other suitable treatment, and returned to the alkylation reactor.

To regenerate the alkylation catalyst, at least a portion of the alkylation catalyst of the alkylation reaction system is passed to a stripping vessel for separating such alkylation catalyst into a stripper overhead stream and a stripper bottoms stream. This portion of the alkylation catalyst can also be referred to as a slip stream. This slip stream contains the hydrogen fluoride and sulfone catalyst mixture along with a concentration of the ASO reaction by-product which has accumulated in the alkylation catalyst.

It is important for the proper operation of the alkylation reaction process to maintain a reasonably low concentration of acid soluble oil in the alkylation catalyst. Thus, the ASO concentration should not exceed 10 weight percent of the alkylation catalyst. Preferably, the ASO concentration is less than 7.5 weight percent and, most preferably, the ASO concentration is less than 5 weight percent. Thus, the ASO concentration will generally be in the range of 0.25 weight percent to 10 weight percent, but specifically, it can be in the range from 0.5 weight percent to 7.5 weight percent. More specifically, it will be in the range from 0.75 weight percent to 5 weight percent.

The slip stream is passed or charged to a stripping column, which defines a separation zone and provides means for separating the alkylation catalyst into a stripper bottoms stream and a stripper overhead stream. It is preferred for the stripping means to be a standard separation column which utilizes hot vaporous isobutane as a stripping fluid. Thus, when stripping isobutane is used, the stripper overhead stream contains hydrogen fluoride and isobutane and the stripper bottoms stream contains sulfone and ASO reaction by-product.

The stripper bottoms stream from the stripping column primarily contains sulfone and ASO. The sulfone component of the stripper bottoms stream represents at least 90 percent of the sulfone contained in the slip stream charged to the stripping column. Preferably, the sulfone in the stripper bottoms stream will contain at least 92.5 percent of the sulfone in the slip stream feed and, most preferably, it will represent at least 95 percent of the sulfone in the slip stream feed.

Due to the inability of the stripping column to separate all of the HF from the sulfone of the slip stream, some HF can pass with the stripper bottoms stream. While it is preferable to minimize the HF concentration in the stripper bottoms stream, it generally can be in the range of from about 5 weight percent to about 40 weight percent. More specifically, the HF concentration in the stripper bottoms stream can range from about 8 weight percent to about 30 weight percent and, most specifically, the HF concentration can range from 10 weight percent to 20 weight percent.

In order to reuse the sulfolane of the stripper bottoms stream as a component of the alkylation catalyst, the ASO must be separated therefrom. The prior art suggests that a mixture of sulfone and ASO may be separated into an ASO-enriched phase and a sulfone-enriched phase simply by cooling and gravity separation. The prior art also suggests that such a separation of the sulfone and ASO mixture occurs even when there is upwardly to about 30 weight percent HF present.

It has been discovered that a more efficient separation of the ASO from the sulfone and ASO mixture can be achieved by use of isobutane as an additive to the stripper bottoms stream. Thus, a critical aspect of the inventive process is the provision of a concentration of isobutane in the stripper bottoms stream in an amount that is effective in promoting the subsequent formation of at least two liquid phases including an upper phase and a lower phase with the upper phase containing a major portion of isobutane admixed with the stripper bottoms stream and light ASO and the lower phase containing sulfone and heavy ASO.

It has been found that the use of isobutane in the stripper bottoms stream promotes the separation of ASO from the sulfone when the stripper bottoms stream has a concentration of HF and even when such HF concentration is significant. While a significant concentration level of HF in the mixture of sulfone and ASO inhibits the formation of two separate liquid phases, the use of isobutane permits the separation of ASO, particularly, light ASO, from the sulfone and forming the upper phase and the lower phase, which further includes HF.

The inventive method includes providing a concentration of isobutane in the stripper bottoms stream containing sulfone, ASO and, optionally, HF at concentrations as hereinabove described. The provided concentration of isobutane must be effective for promoting the subsequent formation of at least two liquid phases, but it is critical for the provided isobutane to be at least about 10 volume percent of the stripper bottoms stream. Thus, the concentration of isobutane provided with the stripper bottoms stream can be in the range of from about 10 volume percent to about 50 volume percent. Preferably, such isobutane concentration can be in the range of from about 15 volume percent to about 45 volume percent and, most preferably, it can be in the range of from 20 volume percent to 40 volume percent.

Any suitable method can be used to provide the isobutane with the stripper bottoms stream including directly admixing isobutane with the stripper bottoms stream. But, another method may include the adjustment of the stripping column operation so as to provide the stripper bottoms stream having a desired isobutane concentration. In any event, it is a critical aspect of the inventive method for the isobutane to be present in the stripper bottoms stream.

The stripper bottoms stream, having the required concentration of isobutane, undergoes a separation whereby at least two liquid phases are formed including an upper phase and a lower phase. The upper phase includes ASO, particularly light ASO, and a major portion of the isobutane contained in the stripper bottoms stream, and the lower phase includes sulfone and heavy ASO. When there is HF present in the stripper bottoms stream, the lower phase can further include HF.

In order to provide for sulfone that can suitably be used in the alkylation catalyst, the lower phase undergoes a separation to separate it into an overhead product, containing sulfone, and a bottoms product containing the heavy ASO of the lower phase. If the stripper bottoms stream contains HF, the overhead product can further include HF. To minimize the amount of thermal decomposition of sulfone during the separation of the lower phase, it is important for the separation of the lower phase to be conducted by vacuum distillation. The overhead product from the vacuum distillation step can be reused by adding it to the alkylation catalyst.

Now referring to FIG. 1, there is depicted by schematic representation an alkylation process system 10. A hydrocarbon feed mixture, comprising olefins and isoparaffins, is introduced into riser-reactor 12 through conduit 14. Riser-reactor 12 defines a reaction zone wherein the hydrocarbon feed mixture is contacted, or admixed, with an alkylation catalyst mixture, comprising sulfolane and hydrogen fluoride, in order to produce a reaction product and a reaction by-product. The olefins of the hydrocarbon feed mixture generally comprise one or more olefins having from three to five carbon atoms, and the isoparaffins of the hydrocarbon feed mixture generally will have from four to six carbon atoms. The alkylation catalyst mixture is introduced into riser-reactor 12 via conduit 16.

The admixture of hydrocarbon feed mixture and alkylation catalyst mixture passes through the reaction zone defined by riser-reactor 12 wherein a reaction takes place in which the olefins of the hydrocarbon feed mixture react with isoparaffins of the hydrocarbon feed mixture to produce an alkylate reaction product. Also, within the reaction zone, the alkylation reaction by-product, ASO, is formed.

The reactor effluent, which includes the alkylate product and reaction by-product, from riser-reactor 12 passes to settler vessel 18, which defines a separation zone for separating the alkylate reaction product from the alkylation catalyst mixture to produce a separated reaction product 20 and a separated alkylation catalyst phase 22. The separated alkylation catalyst phase 22 contains a portion, but, preferably, a substantial portion, of the alkylation reaction by-product, ASO. The separated reaction product 20 passes to downstream processing via conduit 24. The separated alkylation catalyst phase 22 can be recycled via conduits 26 and 16 to riser-reactor 12 for reuse as the alkylation catalyst mixture. Interposed in conduit 26 is catalyst cooler 28, which defines a heat transfer zone for exchanging heat from separated alkylation catalyst phase 22 to a heat transfer fluid such as water.

In order to regenerate the separated alkylation catalyst phase by removing accumulated ASO, a portion, sometimes referred to as a slip stream or a drag stream, of the separated alkylation catalyst phase 22 passes by way of conduit 30 to stripping column 32. Stripping column 32 defines a separation zone including an intermediate zone positioned between an upper flash zone and a lower stripping zone. Stripping column 32 provides means for stripping HF from the slip stream of alkylation catalyst charged thereto and to provide a stripper bottoms stream and a stripper overhead stream.

Introduced into stripping column 32 by way of conduit 38 is vaporous isobutane which provides energy for separating the slip stream into the stripper overhead stream and the stripper bottoms stream and, more specifically, for stripping the hydrogen fluoride from the slip stream. The stripper overhead stream passes from stripping column 32 by way of conduit 40 to settler vessel 18. The stripper bottoms stream passes from stripping column 32 by way of conduit 42 to phase separator, or decanter, 44. Interposed in conduit 42 is heat exchanger 46, which provides for the cooling by indirect heat exchange of the stripper bottoms stream prior to feeding the cooled stripper bottoms stream to decanter 44. Decanter 44 defines a separation zone and provides for the separation of the cooled stripper bottoms stream into an upper phase 46 and a lower phase 48.

Critical to the inventive method is the provision of isobutane into the stripper bottoms stream. Isobutane can be introduced into the stripper bottoms stream by way of conduit 50. Another approach to providing isobutane into the stripper bottoms is to adjust the operation of stripping column 32 so as to provide the desired amount of isobutane in the stripper bottoms stream. In any event, the isobutane and/or other light paraffins are required for the formation of the two liquid phases in decanter 44 and for the enhancement of ASO recovery in upper phase 46. Upper phase 46 contains light ASO and a major portion of the isobutane of the stripper bottoms stream. Upper phase 46 passes from decanter 44 by way of conduit 52. Lower phase 48 contains sulfolane, heavy ASO and, if there is HF present in the stripper bottoms stream, HF. Lower phase 48 passes from decanter 44 through conduit 54 and is charged to vacuum fractionator 56.

Vacuum fractionator 56 defines a separation zone and provides means for separating lower phase 48 into an overhead product containing sulfolane and a bottoms product containing heavy ASO. The overhead product can further contain HF. The overhead product passes from vacuum fractionator 56 through conduit 58 to settler vessel 18 wherein it is recombined with separated alkylation catalyst phase 22 for reuse as a component of the alkylation catalyst. The bottoms product passes from vacuum fractionator 56 by way of conduit 60.

The following examples demonstrate the advantages of the present invention. These examples are for illustration purposes only, and they are not intended to limit the invention as set out in the appended claims.

EXAMPLE I

Samples were taken from the upper phase (Sample #1) and lower phase (Sample #2) of a decanter separator of an experimental process unit having a process flow similar to that as described in FIG. 1. A stripper bottoms stream containing sulfolane, ASO, hydrocarbons and HF was passed to the decanter separator in which the upper phase and lower phase were formed. The hydrocarbon included predominantly isobutane, but it also included other hydrocarbons such as alkylate having eight or more carbon atoms.

A portion of Sample #1 was removed for titration. This portion was partially neutralized with sodium hydroxide solution, and the resultant partially neutralized sample portion was titrated to the phenolpthalein endpoint with standard NaOH solution. The sample portion was non-fuming and the titration results indicated $\leq 2$ percent HF present.

A second, larger portion of Sample #1 (86.81 g) was removed for ASO extraction. This material was extracted twice with 200 mL n-pentane. The n-pentane extracts were washed with distilled water, then dried over a minimal amount of anhydrous magnesium sulfate (to adsorb free water), and filtered. The filtrate was collected in a tared flask, and the n-pentane was removed by rotary evaporation. Following bulk solvent removal, the last traces of solvent were removed by placing in a vacuum oven at 40° C. and ≦10 mm Hg pressure for one hour. A total of 74.00 g ASO was collected (85.2 percent ASO by weight).

A third portion of Sample #1 (278.54 g) was placed into a suitable sample cylinder and cooled to −78° C. The cylinder was evacuated and attached to a second cylinder also cooled to −78° C. The vacuum source was blocked and the cylinder containing Sample #1 was allowed to warm slowly to room temperature, allowing the collection of volatiles in the second cylinder. After three hours, the second cylinder was removed and weighed. A total of 47.66 grams of volatiles were collected. These volatiles were passed over a bed of alumina beads (¼"diameter) to adsorb any HF present. After scrubbing, the sample was analyzed by gas chromatography. The results of the GC analysis are given in Table I.

TABLE I

| GC Analysis of Volatiles Fraction: Sample #1 | |
| --- | --- |
| Component | GC Area % |
| $C_3$ | 3.94 |
| $iC_4$ | 87.74 |
| $nC_4$ | 4.49 |
| $iC_5$ | 2.67 |
| $C_6+$ | 1.01 |

The results from analysis of Sample #1 indicate that it contained less than 2 percent HF, 85.2 percent ASO with the remainder being mostly hydrocarbons. An analysis of the volatile fraction of Sample #1 presented in Table I indicates that the volatile fraction was enriched in isobutane and contained only a small portion of heavier hydrocarbons having six or more carbon atoms.

Sample #2 was treated in a similar manner as Sample #1. Titration results (3 replicates) showed 15.0 percent HF by weight. A second portion of Sample #2 (133.9 g) was extracted with n-pentane in order to isolate the ASO. A total of 9.92 gASO was obtained, indicating 7.41 percent ASO by weight. A third portion of Sample #2 was removed and the volatile portion was collected at −78° C. as described above for Sample #1. Only a trace of volatile material was collected (~1 g) and was analyzed by GC. The GC analysis is summarized in Table II.

TABLE II

| GC Analysis of Volatiles Fraction: Sample #2 | |
| --- | --- |
| Component | GC Area % |
| $iC_4$ | 4.67 |
| $nC_4$ | 1.30 |
| $iC_5$ | 10.2 |
| $C_6+$ | 83.8 |

The results from the analysis of Sample #2 indicate that it contained a substantial fraction of sulfolane with 15 percent HF, 7.41 percent ASO and a small volatile fraction. As the data of Table II show, only a small portion of the volatile fraction was isobutane. A comparison of the compositions of Sample #1 and Sample #2 shows that isobutane preferentially passes into the upper, ASO-rich phase of the decanter separator while the heavier hydrocarbons and sulfolane preferentially pass into the lower phase. Thus, the upper phase contains a substantial portion of the ASO in the decanter separator feed and a major portion of the isobutane in the decanter separator feed.

Figure 2:
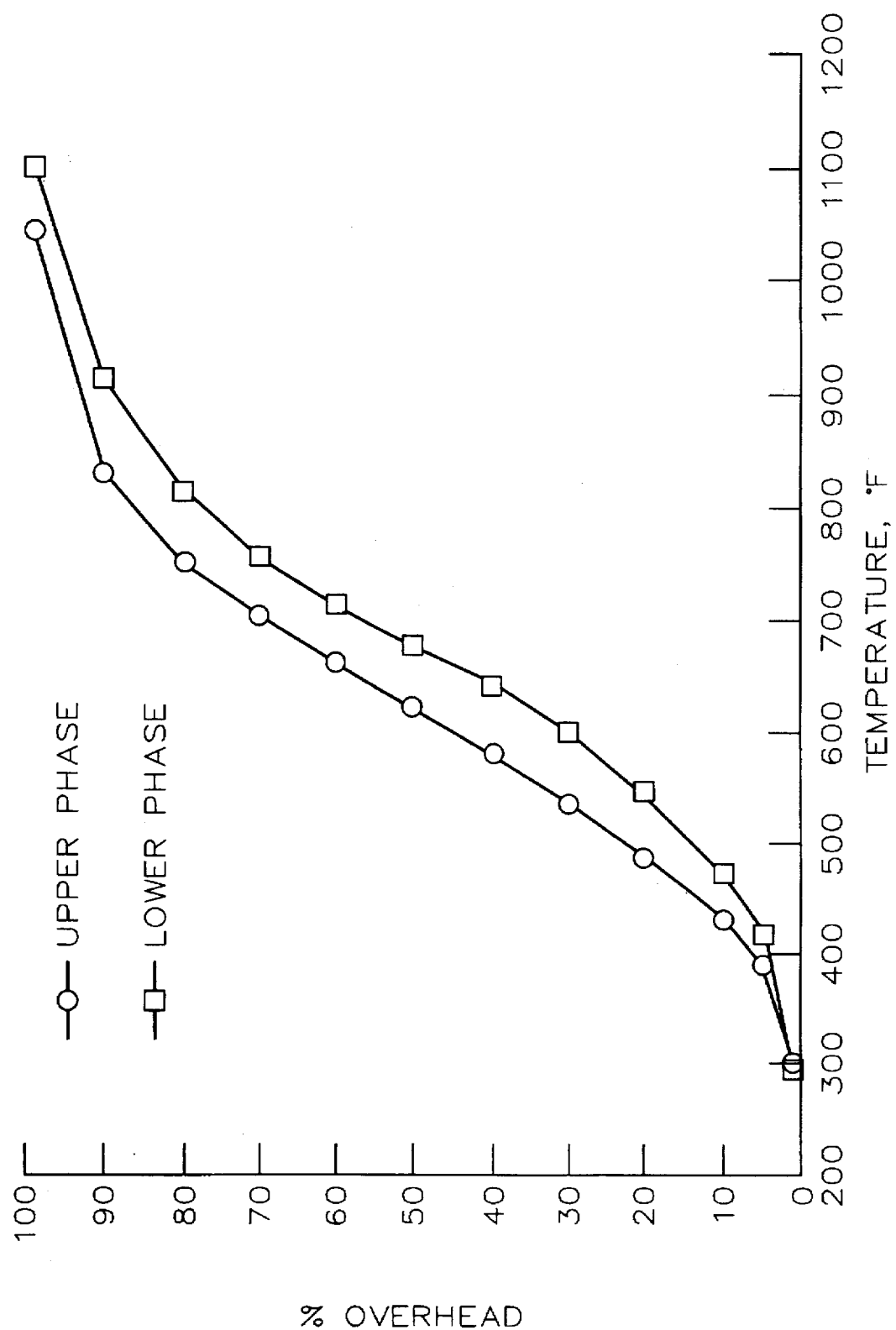
FIG. 2 presents simulated distillation curves for a light ASO taken from the upper phase of the inventive process and a heavy ASO taken from the lower phase of the inventive process.

A simulated distillation of each of the ASO samples taken from the decanter separator upper phase (Sample #1) and the decanter separator lower phase (Sample #2) was performed to determine their distillation characteristics. Their simulated distillation curves are presented in FIG. 2. As can be observed, the ASO of the upper phase is lighter in character than the ASO from the lower phase thus showing that the lighter ASO preferentially enters into the upper phase while the heavier ASO preferentially enters the lower phase of the separator.

EXAMPLE II

Standard solutions of HF, ASO, sulfolane, and water were prepared in the laboratory, using ASO obtained from a Phillips Petroleum Company alkylation process unit located at Sweeny, Tex. The solutions contained 12 percent HF and had a 9/1 ratio by weight of sulfolane to ASO. The solutions were then placed into a separatory funnel and extracted with alkylate (no butane) using a 3/1 and 0.33/1 volumetric ratio of alkylate to mixture. In Table III the results from these extractions are presented. It is apparent that the best extractive efficiency (10.5 percent ASO recovery) is much poorer than that described in Example I above. These data show that the use of isobutane is required for an effective ASO enrichment of the upper decanter phase.

TABLE III

| ASO Extraction by Alkylate | | | |
| --- | --- | --- | --- |
| Phase | Alkylate/Mix Ratio | ASO Extracted (g) | % of Total ASO |
| Upper | 3 | 0.42 | 10.5 |
| Lower | 3 | 3.56 | 89.5 |
| Upper | 0.33 | 0.47 | 2.88 |
| Lower | 0.33 | 15.9 | 97.1 |

While this invention has been described in terms of the presently preferred embodiment, reasonable variations and modifications are possible by those skilled in the art. Such variations and modifications are within the scope of the described invention and the appended claims.

That which is claimed:

1. A method for regenerating an alkylation catalyst mixture used in an alkylation process system, said method comprises the steps of:

alkylating an isoparaffin with an olefin in the presence of said alkylation catalyst mixture, containing HF and sulfolane, in an alkylation reaction zone thereby forming an alkylate product and an ASO reaction by-product containing light ASO and heavy ASO;

passing an alkylation reaction zone effluent, containing said alkylate product and said ASO reaction by-product, from said alkylation reaction zone to a separation zone for separating said alkylation reaction zone effluent into a hydrocarbon phase, containing said alkylate product, and an alkylation catalyst mixture phase, containing said alkylation catalyst mixture and said ASO reaction by-product;

passing at least a portion of said alkylation catalyst mixture phase to means for stripping HF from said at least a portion of said alkylation catalyst mixture phase to provide a stripper bottoms stream and a stripper overhead stream with said stripper overhead stream containing HF and said stripper bottoms stream containing sulfolane and said ASO reaction by-product;

combining said stripper bottoms stream with an isobutane stream thereby forming an isobutane-stripper bottoms stream, said isobutane-stripper bottoms stream comprising a concentration of at least about 10 volume percent isobutane:

separating said isobutane-stripper bottoms stream into at least two liquid phases including an upper phase and a lower phase wherein said upper phase includes a major portion of the isobutane of said isobutane-stripper bottoms stream and light ASO and said lower phase includes sulfolane and heavy ASO;

separating said lower phase by vacuum distillation to provide an overhead product containing sulfolane and a bottoms product containing heavy ASO; and adding said overhead product to said alkylation catalyst mixture phase.

2. A method as recited in claim 1, wherein said concentration of isobutane in said isobutane-stripper bottoms stream is in the range of from about 15 volume percent to about 45 volume percent.

3. A method as recited in claim 1, wherein said concentration of isobutane in said isobutane-stripper bottoms stream is in the range of from 20 volume percent to 40 volume percent.

4. A method as recited in claim 1, wherein said stripper bottoms stream contains at least 90 percent of the sulfolane in said at least a portion of said alkylation catalyst mixture phase.

5. A method as recited in claim 2, wherein said stripper bottoms stream contains at least 90 percent of the sulfolane in said at least a portion of said alkylation catalyst mixture phase.

6. A method as recited in claim 3, wherein said stripper bottoms stream contains at least 90 percent of the sulfolane in said at least a portion of said alkylation catalyst mixture phase.

7. A method as recited in claim 4, wherein said stripper bottoms stream further contains an HF concentration in the range of from about 5 weight percent to about 40 weight percent.

8. A method as recited in claim 5, wherein said stripper bottoms stream further contains an HF concentration in the range of from about 5 weight percent to about 40 weight percent.

9. A method as recited in claim 6, wherein said stripper bottoms stream further contains an HF concentration in the range of from about 5 weight percent to about 40 weight percent.

10. A method as recited in claim 7, wherein said lower phase further includes HF.

11. A method as recited in claim 8, wherein said lower phase further includes HF.

12. A method as recited in claim 9, wherein said lower phase further includes HF.

13. A method for regenerating an alkylation catalyst mixture used in an alkylation process system, said method comprises the steps of:

alkylating an isoparaffin with an olefin in the presence of said alkylation catalyst mixture, containing HF and sulfolane, in an alkylation reaction zone thereby forming an alkylate product and an ASO reaction by-product containing light ASO and heavy ASO;

passing an alkylation reaction zone effluent, containing said alkylate product and said ASO reaction by-product, from said alkylation reaction zone to a separation zone for separating said alkylation reaction zone effluent into a hydrocarbon phase, containing said alkylate product, and an alkylation catalyst mixture phase, containing said alkylation catalyst mixture and said ASO reaction by-product;

passing at least a portion of said alkylation catalyst mixture phase to means for stripping HF from said at least a portion of said alkylation catalyst mixture phase to provide a stripper bottoms stream and a stripper overhead stream with said stripper overhead stream containing HF and said stripper bottoms stream containing sulfolane and said ASO reaction by-product;

admixing said stripper bottoms stream with isobutane thereby forming an isobutane-stripper bottoms stream, said isobutane-stripper bottoms stream comprising a concentration of at least about 10 volume percent isobutane;

separating said isobutane-stripper bottoms stream into at least two liquid phases including an upper phase and a lower phase wherein said upper phase includes a major portion of the isobutane of said isobutane-stripper bottoms stream and light ASO and said lower phase includes sulfolane and heavy ASO;

separating said lower phase by vacuum distillation to provide an overhead product containing sulfolane and a bottoms product containing heavy ASO; and adding said overhead product to said alkylation catalyst mixture phase.

14. A method as recited in claim 13, wherein said concentration of isobutane in said isobutane-stripper bottoms stream is in the range of from about 15 volume percent to about 45 volume percent.

15. A method as recited in claim 13, wherein said concentration of isobutane in said isobutane-stripper bottoms stream is in the range of from 20 volume percent to 40 volume percent.

16. A method as recited in claim 13, wherein said stripper bottoms stream contains at least 90 percent of the sulfolane in said at least a portion of said alkylation catalyst mixture phase.

17. A method as recited in claim 14, wherein said stripper bottoms stream contains at least 90 percent of the sulfolane in said at least a portion of said alkylation catalyst mixture phase.

18. A method as recited in claim 15, wherein said stripper bottoms stream contains at least 90 percent of the sulfolane in said at least a portion of said alkylation catalyst mixture phase.

19. A method as recited in claim 16, wherein said stripper bottoms stream further contains an HF concentration in the range of from about 5 weight percent to about 40 weight percent.

20. A method as recited in claim 17, wherein said stripper bottoms stream further contains an HF concentration in the range of from about 5 weight percent to about 40 weight percent.

21. A method as recited in claim 18, wherein said stripper bottoms stream further contains an HF concentration in the range of from about 5 weight percent to about 40 weight percent.

22. A method as recited in claim 19, wherein said lower phase further includes HF.

23. A method as recited in claim 20, wherein said lower phase further includes HF.

24. A method as recited in claim 21, wherein said lower phase further includes HF.

* * * * *